United States Patent
Swaminathan et al.

(10) Patent No.: US 10,662,154 B2
(45) Date of Patent: May 26, 2020

(54) METHODS OF MANUFACTURE OF 2-ARYL-3,3-BIS(4-HYDROXYARYL) PHTHALIMIDINES, AND POLYMERS DERIVED THEREFROM

(71) Applicant: SABIC GLOBAL TECHNOLOGIES B.V., Bergen op Zoom (NL)

(72) Inventors: Shubashree Swaminathan, Karnataka (IN); Shivakumar Konda, Karnataka (IN); Gaurav Mediratta, Karnataka (IN)

(73) Assignee: SABIC GLOBAL TECHNOLOGIES B.V., Bergen op Zoom (NL)

(*) Notice: Subject to any disclaimer, the term of this patent is extended or adjusted under 35 U.S.C. 154(b) by 24 days.

(21) Appl. No.: 16/095,259

(22) PCT Filed: Apr. 20, 2017

(86) PCT No.: PCT/IB2017/052288
§ 371 (c)(1),
(2) Date: Oct. 19, 2018

(87) PCT Pub. No.: WO2017/182984
PCT Pub. Date: Oct. 26, 2017

(65) Prior Publication Data
US 2019/0135748 A1    May 9, 2019

Related U.S. Application Data

(60) Provisional application No. 62/326,065, filed on Apr. 22, 2016.

(51) Int. Cl.
*C07D 209/46* (2006.01)
*B01J 31/02* (2006.01)
*C08G 64/06* (2006.01)

(52) U.S. Cl.
CPC ........ *C07D 209/46* (2013.01); *B01J 31/0238* (2013.01); *B01J 31/0244* (2013.01); *C08G 64/06* (2013.01)

(58) Field of Classification Search
USPC .......................................................... 528/211
See application file for complete search history.

(56) References Cited

U.S. PATENT DOCUMENTS

| 7,348,439 | B2 | 3/2008 | Ganesan et al. |
| 2007/0123714 | A1 | 5/2007 | Ganesan et al. |
| 2008/0242829 | A1 | 10/2008 | Basale et al. |

FOREIGN PATENT DOCUMENTS

WO    2015162564 A1    10/2015

OTHER PUBLICATIONS

International Search Report; International Application No. PCT/IB2017/052238; International Filing Date—Apr. 20, 2017; dated Aug. 4, 2017; 5 pages.
Written Opinion for International Application No. PCT/IB2017/052283; International Filing Date—Apr. 20, 2017; dated Aug. 4, 2017; 8 pages.

*Primary Examiner* — Terressa Boykin
(74) *Attorney, Agent, or Firm* — Cantor Colburn LLP

(57) ABSTRACT

A method for the manufacture of a 2-aryl-3,3-bis(hydroxyaryl)phthalimidine including heating a reaction mixture comprising a phenolphthalein compound and a primary arylamine in the presence of an acid catalyst, and a heterocyclic aromatic amine co-catalyst, to form the 2-aryl-3,3-bis(hydroxyaryl) is provided. Polymers including structural units derived from the 2-aryl-3,3-bis(hydroxyaryl)phthalimidine are provided. Methods for the manufacture of a polycarbonate, including manufacturing the 2-aryl-3,3-bis(hydroxyaryl)phthalimidine, and polymerizing the 2-aryl-3,3-bis(hydroxyaryl)phthalimidine in the presence of a carbonate source are provided.

21 Claims, No Drawings

METHODS OF MANUFACTURE OF 2-ARYL-3,3-BIS(4-HYDROXYARYL) PHTHALIMIDINES, AND POLYMERS DERIVED THEREFROM

CROSS REFERENCE TO RELATED APPLICATIONS

This application is a National Stage application of PCT/IB2017/052288, filed Apr. 20, 2017, which claims the benefit of U.S. Provisional Application No. 62/326,065, filed Apr. 22, 2016, the disclosures of which are incorporated by reference in their entirety herein.

BACKGROUND

There is a need for methods for the production of 2-phenyl-3,3-bis(4-hydroxyphenyl)phthalimidine (also known as N-phenyl phenolphthalein bisphenol (PPPBP) or 3,3-bis(4-hydroxyphenyl)-2-phenylisoindolin-1-one)) wherein the as-synthesized product contains reduced amounts of an aminophenol, or no aminophenol.

BRIEF SUMMARY

A method for the manufacture of a 2-aryl-3,3-bis(hydroxyaryl)phthalimidine of formula (I)

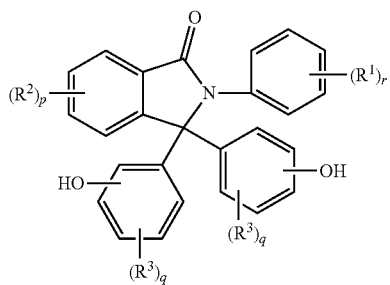

(I)

the method comprising: heating a reaction mixture comprising a phenolphthalein compound of formula (II):

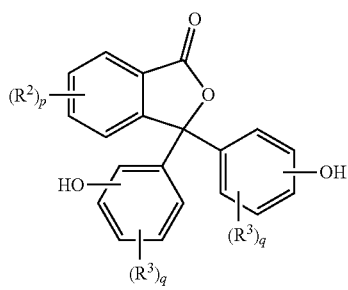

(II)

and a primary arylamine of formula (III):

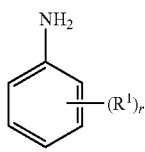

(III)

in the presence of an acid catalyst, and a heterocyclic aromatic amine co-catalyst, to form the 2-aryl-3,3-bis(hydroxyaryl)phthalimidine of formula (I), wherein in formulas (I), (II), and (III), each occurrence of $R^1$ is the same or different, and is a phenyl or a $C_{1-25}$ hydrocarbyl, preferably a phenyl or a $C_{1-6}$ alkyl, more preferably a $C_{1-3}$ alkyl, each occurrence of $R^2$ and $R^3$ is independently a $C_{1-25}$ hydrocarbyl or halogen, preferably a $C_{1-6}$ alkyl, more preferably a $C_{1-3}$ alkyl, and r, p, and q are each independently 0 to 4, more preferably 0 or 1, preferably 0 is provided.

2-aryl-3,3-bis(4-hydroxyaryl)phthalimidines produced by the described method are also provided.

A 2-aryl-3,3-bis(4-hydroxyaryl) phthalimidine composition, comprising an as-synthesized phthalimidine of formula (I)

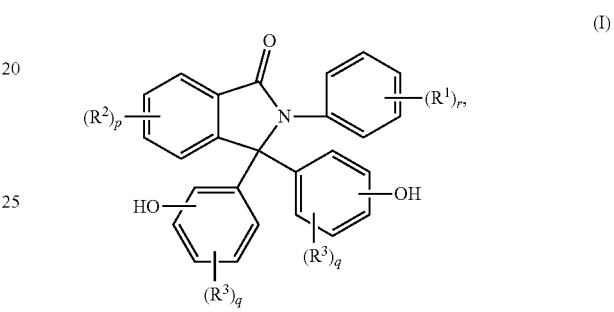

(I)

wherein each occurrence of $R^1$ is independently a phenyl or $C_{1-25}$ hydrocarbyl, preferably a phenyl or a $C_{1-6}$ alkyl, more preferably a $C_{1-3}$ alkyl, each occurrence of $R^2$ and $R^3$ is independently a $C_{1-25}$ hydrocarbyl or halogen, preferably a $C_{1-6}$ alkyl, more preferably a $C_{1-3}$ alkyl, and r, p, and q are each independently 0 to 4, more preferably 0 or 1, preferably 0; 500 to 8000 parts per million of an aminophenol, preferably 800 to 5000, more preferably from 400 to 1400 parts per million of an aminophenol; and 0 to 1000 parts per million of a phenolphthalein compound of formula (II), preferably 0 to 500 parts per million of a phenolphthalein compound of formula (II).

Polycarbonates and other polymers prepared from the 2-aryl-3,3-bis(4-hydroxyaryl)phthalimidines produced by the described method are also provided.

A method for the manufacture of a polycarbonate, comprising manufacturing the 2-aryl-3,3-bis(4-hydroxyaryl) phthalimidine of formula (I) by the described method, and polymerizing the 2-aryl-3,3-bis(4-hydroxyaryl) phthalimidine of formula (I) in the presence of a carbonate source is also provided.

The above described and other features are exemplified by the following detailed description.

DETAILED DESCRIPTION

The present disclosure is generally directed to producing phenolphthalein derivatives, in particular 2-aryl-3,3-bis(4-hydroxyaryl)phthalimidines, which are suitable for use as monomers or comonomers for preparing polycarbonates and other polymers. The method generally uses an acid catalyst and a heterocyclic aromatic amine co-catalyst.

Provided is a synthetic route for producing 2-phenyl-3,3-bis(4-hydroxyphenyl)phthalimidine (PPPBP) and other 2-aryl-3,3-bis(4-hydroxyaryl)phthalimidines using a heterocyclic aromatic amine as a co-catalyst. This process can minimize aminophenol impurity formation, thereby eliminating or reducing the existing downstream purification using activated carbon/acidic ion exchange resin as an adsorbent for removing the aminophenol impurity. The reaction kinetics can also be improved using the new procedures. The procedures in the method for forming PPPBP are further described below.

The 2-aryl-3,3-bis(4-hydroxyaryl)phthalimidines produced in accordance with these methods can be used in the manufacture of polycarbonates and other polymers. The 2-aryl-3,3-bis(4-hydroxyaryl)phthalimidines produced in accordance with these methods can have improved properties, such as a lower level of aminophenol impurity. The methods described to manufacture and purify 2-aryl-3,3-bis(4-hydroxyaryl)phthalimidines can further have a shorter reaction time as compared to previous methods, as well as reducing or eliminating the need for carbon adsorbents for impurity removal.

The 2-aryl-3,3-bis(4-hydroxyaryl)phthalimidines produced in accordance with this disclosure are of formula (I):

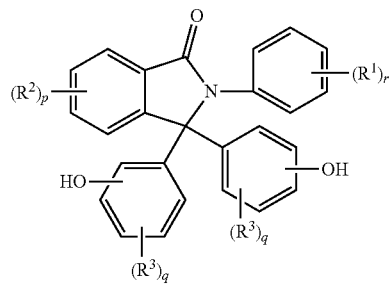

wherein each $R^1$ is independently a phenyl or a $C_{1-25}$ hydrocarbyl, preferably a phenyl or a $C_{1-6}$ alkyl, more preferably a $C_{1-3}$ alkyl, each $R^2$ and $R^3$ is independently a hydrogen, a $C_{1-25}$ hydrocarbyl or halogen, preferably a $C_{1-6}$ alkyl, more preferably a $C_{1-3}$ alkyl, and r, p, and q are each independently 0 to 4, more preferably 0 or 1, preferably 0. In some embodiments, $R^1$ is phenyl or a $C_{1-3}$ alkyl group, and $R^2$ is hydrogen, a $C_{1-3}$ alkyl group, or a halogen.

A preferred 2-aryl-3,3-bis(4-hydroxyaryl)phthalimidine is of formula (IA)

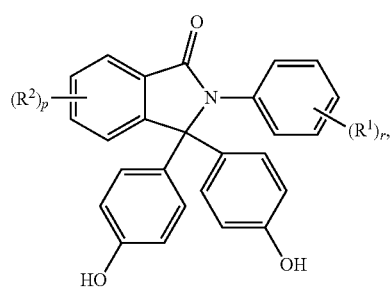

wherein $R^1$ is a phenyl or a $C_{1-3}$ alkyl, $R^2$ is a hydrogen, a $C_{1-3}$ alkyl or a halogen, p is 0 or 1, and r is 0 or 1; preferably wherein each of p and r is zero. A preferred 2-aryl-3,3-bis(4-hydroxyaryl)phthalimidine is 2-phenyl-3,3-bis(4-hydroxyphenyl)-2-phthalimidine.

The 2-aryl-3,3-bis(4-hydroxyaryl)phthalimidine of formula (I) can be prepared by the reaction of a primary arylamine, e.g., an aniline, of formula (III):

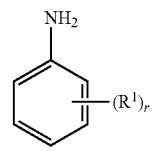

wherein $R^1$ is defined above and r is as defined above; with a phenolphthalein compound of formula (II):

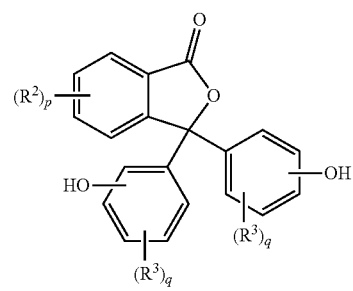

wherein $R^2$, $R^3$, p and q are as defined above. An acid catalyst and a heterocyclic aromatic amine co-catalyst are generally used to facilitate formation of the phthalimidine compound.

The as-synthesized 2-aryl-3,3-bis(hydroxyaryl)phthalimidine of formula (I) comprises 500 to 8000 parts per million of an aminophenol, for example an aminophenol of the formula

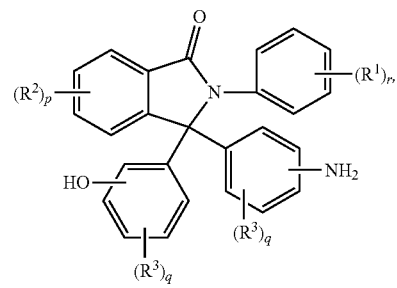

where the variables are as defined above, preferably 800 to 5000, more preferably 400 to 1400 parts per million of an aminophenol. As-synthesized means the compound as precipitated from the reaction mixture before any additional purification. The 2-aryl-3,3-bis(hydroxyaryl)phthalimidine of formula (I) comprises zero to 1000 parts per million of the phenolphthalein compound of formula (II), preferably zero to 500 parts per million of the phenolphthalein compound of formula (II). In an embodiment, the 2-aryl-3,3-bis(hydroxyaryl)phthalimidine of formula (I) comprises less than 1000 parts per million of the phenolphthalein compound of formula (II), preferably less than 500 parts per million of the phenolphthalein compound of formula (II)

Exemplary primary arylamines include aniline. In some embodiments, the primary arylamine is present at a concentration of 3.0-5.0 molar equivalents of the phenolphthalein compound of formula (II).

The heterocyclic aromatic amine has 5 to 10, preferably 5 to 6 atoms in the ring, and is unsubstituted or substituted with a halogen, nitro, cyano, $C_{1-6}$ alkyl, $C_{3-6}$ cycloalkyl, $C_{2-6}$ alkenyl, $C_{2-6}$ alkynyl, $C_{1-6}$ alkoxy, $C_{1-6}$ alkoxycarbonyl, $C_{6-10}$ aryl, $C_{6-10}$ aryloxy, $C_{7-10}$ alkylarylene, $C_{7-10}$ arylalkylene, —NR'$_2$ wherein each W is the same or different and is a hydrogen, $C_{1-6}$ alkyl, $C_{6-10}$ aryl, $C_{7-10}$ alkylarylene, or $C_{7-10}$ arylalkylene, or two adjacent carbon atoms are substituted with a divalent moiety having from 3 to 4 atoms to form a fused aromatic ring wherein 1 or 2 of the atoms can be a nitrogen, or a combination comprising at least one of the foregoing substituents, preferably wherein the ring is unsubstituted or substituted with a $C_{1-3}$ alkyl, $C_{1-3}$ alkoxy, $C_{1-3}$ alkoxycarbonyl, $C_{6-10}$ aryl, $C_{6-10}$ aryloxy, $C_{7-10}$ alkylarylene, $C_{7-10}$ arylalkylene, NR'$_2$ wherein each R' is the same or different and is a hydrogen, $C_{1-3}$ alkyl, $C_6$ aryl, $C_{7-10}$ alkylarylene, or $C_{7-10}$ arylalkylene, or two adjacent carbon atoms are substituted with a divalent moiety having from 3 to 4 carbon atoms to form a fused aromatic ring, or a combination comprising at least one of the foregoing substituents; preferably wherein the heterocyclic aromatic amine is a pyrrole, an imidazole, a pyridine, an oxazole, an isoxazole, a thiazole, an azocine, an azecine, a quinolone, an isoquinoline, a purine, a carbazole, or a pyrimidine, wherein each of the foregoing can be unsubstituted or substituted with a halogen, nitro, cyano, $C_{1-6}$ alkyl, $C_{2-6}$ alkenyl, $C_{2-6}$ alkynyl, $C_{1-6}$ alkoxy, $C_{1-6}$ alkoxycarbonyl, $C_{6-10}$ aryl, $C_{6-10}$ aryloxy, $C_{7-10}$ alkylarylene, $C_{7-10}$ arylalkylene, —NR'$_2$ wherein each R' is the same or different and is a hydrogen, $C_{1-6}$ alkyl, $C_{6-10}$ aryl, $C_{7-10}$ alkylarylene, or $C_{7-10}$ arylalkylene, or two adjacent carbon atoms are substituted with a divalent moiety having from 3 to 4 carbon atoms to form a fused aromatic ring, or a combination comprising at least one of the foregoing, preferably wherein the ring is unsubstituted or substituted with a $C_{1-3}$ alkyl, $C_{1-3}$ alkoxy, $C_{1-3}$ alkoxycarbonyl, $C_{6-10}$ aryl, $C_{6-10}$ aryloxy, $C_{7-10}$ alkylarylene, $C_{7-10}$ arylalkylene, —NR'$_2$ wherein each R' is the same or different and is a hydrogen, $C_{1-3}$ alkyl, $C_6$ aryl, $C_{7-10}$ alkylarylene, or $C_{7-10}$ arylalkylene, or two adjacent carbon atoms are substituted with a divalent moiety having from 3 to 4 carbon atoms to form a fused aromatic ring, or a combination comprising at least one of the foregoing; preferably wherein the heterocyclic aromatic amine is unsubstituted pyridine, unsubstituted imidazole, or a 4-dimethyl-aminopyridine.

Examples of heterocyclic aromatic amine compounds are a pyrrole, an imidazole, an oxazole, an isoxazole, a thiazole, a pyridine, a pyrimidine, 4-dimethyl-aminopyridine, an azocine, or an azecine, and fused structures such as quinoline, isoquinoline, purine, or carbazole. The heterocyclic aromatic amine can be present at a concentration of 0.005-0.5 molar equivalents of the phenolphthalein compound of formula (II), preferably a concentration of 0.01 to 0.2 molar equivalents of the phenolphthalein compound of formula (II).

Exemplary acid catalysts include mineral acids, including hydrochloric acid. Amine salts of mineral acids can be formed from the reaction of mineral acids with amines. Examples of suitable amines for forming the acid catalysts include primary, secondary, and tertiary amines having any combination of aliphatic and aromatic groups bonded to the amine nitrogen. The mineral acids used for preparing the amine salts can be present in a fluid phase, for example, in a gaseous phase or in a liquid phase or in a combination of the gaseous and liquid phases. Non-limiting examples of mineral acids include hydrogen chloride liquid, hydrogen chloride gas, sulfuric acid, nitric acid, and the like. The acid catalyst can be present at a concentration of 0.5-1.5 molar equivalents of the phenolphthalein compound of formula (II).

Exemplary amine salt catalysts include primary, secondary, and tertiary amine hydrochlorides. In some embodiments, the acid catalyst is introduced as a pre-formed salt of an amine and a mineral acid into the reactor. In another embodiment, the acid catalyst is generated in the reactor by first charging the amine into the reactor, and then adding about ⅓ to about 1 part by weight of an appropriate mineral acid to phenolphthalein compound. In another embodiment, the acid catalyst is generated in the reactor by first charging the amine and an appropriate mineral acid into the reactor, and then adding the phenolphthalein compound. In still another embodiment, about 0.1 parts to about 0.3 parts by weight of hydrogen chloride gas is introduced into a reactor charged with the amine to form an appropriate amount of the amine hydrochloride catalyst. More hydrochloric acid or more hydrogen chloride gas can also be used, but is generally not required. A solvent can optionally be used to initially form the amine hydrochloride from the primary hydrocarbyl amine. The solvent can then be removed (if desired), and the amine catalyst, e.g., an aryl amine salt, can be added to the reaction mixture. In an embodiment, the acid catalyst is present at a concentration of 0.5-1.5 molar equivalents of the phenolphthalein compound of formula (II).

The reaction of the aryl amine of formula (III) with the phenolphthalein compound of formula (II) forms the desired phenolphthalein derivative, e.g., the phthalimidine compound of formula (I). An excess of the aryl amine over the phenolphthalein compound can be used to keep the reaction proceeding in a forward direction.

The heating can occur at a temperature of 135° C. to 180° C., preferably 140° C. to 175° C., more preferably 135° C. to 150° C. The heating can be for 8 to 40 hours, preferably 8 to 30 hours, more preferably 8 to 17 hours.

In an example, the heating is for 10 to 40 hours at 135 to 150° C., and provides the as-synthesized 2-aryl-3,3-bis(hydroxyaryl)phthalimidine of formula (I) having an aminophenol content of 400 to 1400 parts per million.

The acid catalyst and the primary arylamine can be added to a solvent to form an initial composition; water can be removed from the initial composition to provide a reduced water composition; and the phenolphthalein compound of formula (II) and the co-catalyst can be added to the reduced water composition to provide the reaction mixture.

The phthalimidine of formula (I) can be precipitated from the reaction mixture to provide a crude 2-aryl-3,3-bis(hydroxyaryl)phthalimidine of formula (I). The 2-aryl-3,3-bis(hydroxyaryl)phthalimidine of formula (I) can be purified.

The 2-aryl-3,3-bis(hydroxyaryl)phthalimidine of formula (I) can be of formula (IA)

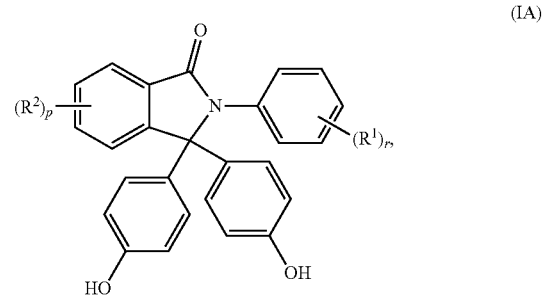

(IA)

wherein $R^1$ is a phenyl or a $C_{1-3}$ alkyl, $R^2$ is a $C_{1-3}$ alkyl or a halogen, p is 0 or 1, and r is 0 or 1; preferably wherein each of p and r is zero, and the phthalimidine of formula (I) is 2-phenyl-3,3-bis(4-hydroxyphenyl)-2-phthalimidine.

In an example, the acid catalyst is hydrochloric acid, the primary arylamine is aniline, the phenolphthalein compound is phenolphthalein, and the heterocyclic aromatic amine co-catalyst is pyridine.

The methods described herein can be used to manufacture a 2-aryl-3,3-bis(4-hydroxyaryl) phthalimidine composition, comprising an as-synthesized phthalimidine of formula (I)

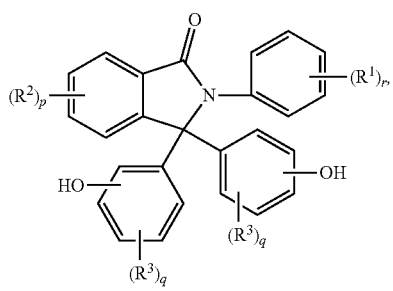

(I)

wherein each occurrence of $R^1$ is independently a phenyl or $C_{1-25}$ hydrocarbyl, preferably a phenyl or a $C_{1-6}$ alkyl, more preferably a $C_{1-3}$ alkyl, each occurrence of $R^2$ and $R^3$ is independently a $C_{1-25}$ hydrocarbyl or halogen, preferably a $C_{1-6}$ alkyl, more preferably a $C_{1-3}$ alkyl, and r, p, and q are each independently 0 to 4, more preferably 0 or 1, preferably 0; 500 to 8000 parts per million of an aminophenol, preferably 800 to 5000 parts per million of an aminophenol, more preferably from 400 to 1400 parts per million of an aminophenol; and zero to 1000 parts per million of a phenolphthalein, preferably zero to 500 parts per million of an phenolphthalein. In an embodiment, the as-synthesized phthalimidine contains less than 1000 parts per million of a phenolphthalein, preferably less than 500 parts per million of a phenolphthalein.

By way of example, the phenolphthalein compound of formula (II) wherein $R^2$ and $R^3$ are H, p and q are 0 was reacted with aniline (formula (III) wherein $R^1$ is H) in the presence of aniline hydrochloride as the acid catalyst, and the presence of pyridine as the heterocyclic aromatic amine co-catalyst to form 2-phenyl-3,3-bis(4-hydroxyphenyl) phthalimidine, shown in formula (IV):

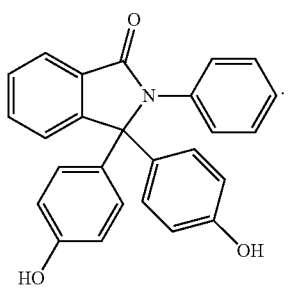

(IV)

In some embodiments, the reaction is conducted at 135° C. to 180° C., preferably from 140-175° C. over a period of less than 10 hours. Water can be removed from the reaction mixture, for example by using an apparatus such as a Dean-Stark apparatus. The acid catalyst, and primary aryl amine can be combined and heated to a temperature above the boiling point of water, for example about 120° C., to remove some or substantially all of the water, prior to addition of the phenolphthalein compound and heterocyclic aromatic amine co-catalyst.

The as-synthesized PPPBP can be produced at high yield (90% to greater than 99%). The purity of the as-synthesized PPPBP can be greater than 95%, preferably 98% or greater. The as-synthesized PPPBP can include from zero to 10000 parts per million of an aminophenol, preferably from zero to 7000 parts per million of an aminophenol. The as-synthesized PPPBP can include less than 1000 parts per million of phenolphthalein, preferably less than 500 parts per million phenolphthalein.

The PPPBP (or other phthalimidines of formula (I)) can be separated and purified by known processes. For example, the PPPBP can be separated from the reaction mixture by precipitation, for example by pouring the reaction mixture into an antisolvent for the phthalimidine compound such as water. For example, the reaction mixture can be stirred into an acidic aqueous solution or into a mixture of ice and a first concentrated acid to precipitate a crude phthalimidine compound. The crude phthalimidine compound can then be isolated, for example by filtration and washing with water. The first acid is not limited and includes hydrochloric acid, sulfuric acid, sulfurous acid, phosphoric acid, and nitric acid. Typically 3 to 9 molar acid is utilized.

The semicrude phthalimidine compound can then isolated from the slurry, for example filtered and washed with dilute acid. The dilute acid can be any of the acids listed above with a concentration from 2 to 6 molar. The semicrude phthalimidine compound can then be washed with water and dried. Drying temperatures can range from 60° C. to 120° C., specifically 67 to 100° C. Drying can occur under vacuum.

A polymer comprising structural units derived from the 2-aryl-3,3-bis(4-hydroxyaryl) phthalimidine manufactured by the methods described herein is also provided. The polymer can be a polycarbonate, preferably wherein the polymer is a copolycarbonate comprising units derived from the 2-aryl-3,3-bis(4-hydroxyaryl) phthalimidine of formula (I) and units derived from bisphenol A. A method for the manufacture of a polycarbonate, includes manufacturing the 2-aryl-3,3-bis(4-hydroxyaryl) phthalimidine of formula (I) in accordance with a method described herein; and polymerizing the 2-aryl-3,3-bis(4-hydroxyaryl) phthalimidine of formula (I) in the presence of a carbonate source The 2-aryl-3,3-bis(4-hydroxyaryl)phthalimidines, including the exemplary 2-phenyl-3,3-bis(4-hydroxyphenyl) phthalimidine (PPPBP), are commercially valuable monomers or comonomers for producing a variety of polymers formed by reactions of the phenolic OH groups of the 2-aryl-3,3-bis(4-hydroxyaryl)phthalimidines. Exemplary polymers that can be produced include homopolymers and copolymers of a polycarbonate, a polyestercarbonate, a polyester, a polyesteramide, a polyimide, a polyetherimide, a polyamideimide, a polyether, a polyethersulfone, a polycarbonate-polyorganosiloxane block copolymer, a copolymer comprising aromatic ester, ester carbonate, and carbonate repeat units, and a polyetherketone. An example of a copolymer comprising aromatic ester, estercarbonate, and carbonate repeat units is the copolymer produced by the reaction of a hydroxy-terminated polyester, such as the product of reaction of isophthaloyl chloride and terephthaloyl chloride with resorcinol, with phosgene and an aromatic dihydroxy compound, such as bisphenol A.

In some embodiments, polycarbonates having low color properties are synthesized, wherein the polycarbonates include structural units of formula (V):

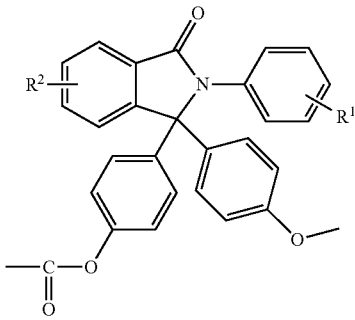

(V)

which are derived from a 2-aryl-3,3-bis(4-hydroxyaryl) phthalimidine of formula (I), wherein $R^1$ and $R^2$ are as described previously; and the C=O structural units are derived from a C=O donor such as a carbonic acid diester in a melt transesterification process, or phosgene in an interfacial process.

Specific polycarbonates are copolycarbonates having structural units derived from a phthalimidine compound of formula (I) and a dihydroxy compound of the formula HO—$R^1$—OH, in particular of formula (VI)

HO-$A^1$-$Y^1$-$A^2$-OH    (VI)

wherein each of $A^1$ and $A^2$ is a monocyclic divalent aromatic group and $Y^1$ is a single bond or a bridging group having one or more atoms that separate $A^1$ from $A^2$. In an exemplary embodiment, one atom separates $A^1$ from $A^2$. Specifically, each $R^1$ can be derived from a dihydroxy aromatic compound of formula (VII):

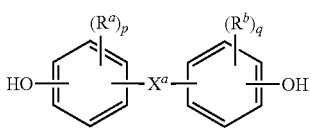

(VII)

wherein $R^a$ and $R^b$ each represent a halogen or $C_{1-12}$ alkyl group and can be the same or different; and p and q are each independently integers of 0 to 4. $X^a$ represents a single bond or a bridging group connecting the two hydroxy-substituted aromatic groups, where the single bond or the bridging group and the hydroxy substituent of each $C_6$ arylene group are disposed ortho, meta, or para (specifically para) to each other on the $C_6$ arylene group. In an embodiment, the bridging group $X^a$ is —O—, —S—, —S(O)—, —S(O)$_2$—, —C(O)—, or a $C_{1-18}$ organic group. The $C_{1-18}$ organic group can be cyclic or acyclic, aromatic or non-aromatic, and can further comprise heteroatoms such as halogens, oxygen, nitrogen, sulfur, silicon, or phosphorous. The $C_{1-18}$ organic group can be disposed such that the $C_6$ arylene groups connected thereto are each connected to a common alkylidene carbon or to different carbons of the $C_{1-18}$ organic group. In some embodiments, p and q is each 1, and $R^a$ and $R^b$ are each a $C_{1-3}$ alkyl group, specifically methyl, disposed meta to the hydroxy group on each arylene group.

In an embodiment, $X^a$ is a substituted or unsubstituted $C_{3-18}$ cycloalkylidene, a $C_{1-25}$ alkylidene of formula —C($R^c$)($R^d$)— wherein $R^c$ and $R^d$ are each independently hydrogen, $C_{1-12}$ alkyl, $C_{1-12}$ cycloalkyl, $C_{7-12}$ arylalkyl, $C_{1-12}$ heteroalkyl, or cyclic $C_{7-12}$ heteroarylalkyl, or a group of the formula —C(=$R^e$)— wherein $R^e$ is a divalent $C_{1-12}$ hydrocarbon group. Exemplary groups of this type include methylene, cyclohexylmethylene, ethylidene, neopentylidene, and isopropylidene, as well as 2-[2.2.1]-bicycloheptylidene, cyclohexylidene, cyclopentylidene, cyclododecylidene, and adamantylidene. In another embodiment, $X^a$ is a $C_{1-18}$ alkylene group, a $C_{3-18}$ cycloalkylene group, a fused $C_{6-18}$ cycloalkylene group, or a group of the formula —$B^1$—W—$B^2$— wherein $B^1$ and $B^2$ are the same or different $C_{1-6}$ alkylene group and W is a $C_{3-12}$ cycloalkylidene group or a $C_{6-16}$ arylene group.

Other useful aromatic dihydroxy compounds of the formula HO—$R^1$—OH include compounds of formula (VIII):

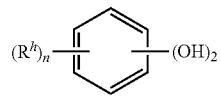

(VIII)

wherein each $R^h$ is independently a halogen atom, a $C_{1-10}$ hydrocarbyl such as a $C_{1-10}$ alkyl group, a halogen-substituted $C_{1-10}$ alkyl group, a $C_{6-10}$ aryl group, or a halogen-substituted $C_{6-10}$ aryl group, and n is 0 to 4. The halogen is usually bromine.

Some illustrative examples of specific aromatic dihydroxy compounds include the following: 4,4'-dihydroxybiphenyl, 1,6-dihydroxynaphthalene, 2,6-dihydroxynaphthalene, bis(4-hydroxyphenyl)methane, bis(4-hydroxyphenyl) diphenylmethane, bis(4-hydroxyphenyl)-1-naphthylmethane, 1,2-bis(4-hydroxyphenyl)ethane, 1,1-bis(4-hydroxyphenyl)-1-phenylethane, 2-(4-hydroxyphenyl)-2-(3-hydroxyphenyl)propane, bis(4-hydroxyphenyl)phenylmethane, 2,2-bis(4-hydroxy-3-bromophenyl)propane, 1,1-bis(hydroxyphenyl)cyclopentane, 1,1-bis(4-hydroxyphenyl)cyclohexane, 1,1-bis(4-hydroxyphenyl)isobutene, 1,1-bis(4-hydroxyphenyl)cyclododecane, trans-2,3-bis(4-hydroxyphenyl)-2-butene, 2,2-bis(4-hydroxyphenyl)adamantane, alpha, alpha'-bis(4-hydroxyphenyl)toluene, bis(4-hydroxyphenyl)acetonitrile, 2,2-bis(3-methyl-4-hydroxyphenyl)propane, 2,2-bis(3-ethyl-4-hydroxyphenyl)propane, 2,2-bis(3-n-propyl-4-hydroxyphenyl)propane, 2,2-bis(3-isopropyl-4-hydroxyphenyl)propane, 2,2-bis(3-sec-butyl-4-hydroxyphenyl)propane, 2,2-bis(3-t-butyl-4-hydroxyphenyl)propane, 2,2-bis(3-cyclohexyl-4-hydroxyphenyl)propane, 2,2-bis(3-allyl-4-hydroxyphenyl)propane, 2,2-bis(3-methoxy-4-hydroxyphenyl)propane, 2,2-bis(4-hydroxyphenyl)hexafluoropropane, 1,1-dichloro-2,2-bis(4-hydroxyphenyl)ethylene, 1,1-dibromo-2,2-bis(4-hydroxyphenyl)ethylene, 1,1-dichloro-2,2-bis(5-phenoxy-4-hydroxyphenyl)ethylene, 4,4'-dihydroxybenzophenone, 3,3-bis(4-hydroxyphenyl)-2-butanone, 1,6-bis(4-hydroxyphenyl)-1,6-hexanedione, ethylene glycol bis (4-hydroxyphenyl)ether, bis(4-hydroxyphenyl)ether, bis(4-hydroxyphenyl)sulfide, bis(4-hydroxyphenyl)sulfoxide, bis (4-hydroxyphenyl)sulfone, 9,9-bis(4-hydroxyphenyl) fluorine, 2,7-dihydroxypyrene, 6,6'-dihydroxy-3,3,3',3'-tetramethylspiro(bis)indane ("spirobiindane bisphenol"), 3,3-bis(4-hydroxyphenyl)phthalimide, 2,6-dihydroxydibenzo-p-dioxin, 2,6-dihydroxythianthrene, 2,7-dihydroxyphenoxathin, 2,7-dihydroxy-9,10-dimethylphenazine, 3,6-dihydroxydibenzofuran, 3,6-dihydroxydibenzothiophene, and 2,7-dihydroxycarbazole, resorcinol, substituted resorcinol compounds such as 5-methyl resorcinol, 5-ethyl resorcinol, 5-propyl resorcinol, 5-butyl resorcinol, 5-t-butyl resorcinol, 5-phenyl resorcinol, 5-cumyl resorcinol, 2,4,5,6-tetrafluoro resorcinol, 2,4,5,6-tetrabromo resorcinol, or the like; catechol; hydroquinone; substituted hydroquinones such as 2-methyl hydroquinone, 2-ethyl hydroquinone, 2-propyl hydroquinone, 2-butyl hydroquinone, 2-t-butyl hydroquinone, 2-phenyl hydroquinone, 2-cumyl hydroquinone, 2,3,5,6-tetramethyl hydroquinone, 2,3,5,6-tetra-t-butyl hydroquinone, 2,3,5,6-tetrafluoro hydroquinone, 2,3,5,6-tetrabromo hydroquinone, or the like, or combinations comprising at least one of the foregoing dihydroxy compounds.

Specific examples of bisphenol compounds of formula (VII) include 1,1-bis(4-hydroxyphenyl) methane, 1,1-bis(4-hydroxyphenyl) ethane, 2,2-bis(4-hydroxyphenyl) propane (hereinafter "bisphenol A" or "BPA"), 2,2-bis(4-hydroxyphenyl) butane, 2,2-bis(4-hydroxyphenyl) octane, 1,1-bis(4-hydroxyphenyl) propane, 1,1-bis(4-hydroxyphenyl) n-butane, 2,2-bis(4-hydroxy-2-methylphenyl) propane, 1,1-bis(4-hydroxy-t-butylphenyl) propane, 3,3-bis(4-hydroxyphenyl) phthalimidine, and 1,1-bis(4-hydroxy-3-methylphenyl)cyclohexane (DMBPC). Combinations comprising at least one of the foregoing dihydroxy compounds can also be used. In one specific embodiment, the polycarbonate is a linear homopolymer derived from bisphenol A, in which each of $A^1$ and $A^2$ is p-phenylene and $Y^1$ is isopropylidene in formula (3).

Exemplary carbonic acid diesters useful in the formation of the polycarbonates in a melt transesterification process are of formula (IX):

$$(ZO)_2C=O \qquad (IX)$$

wherein each Z is independently an unsubstituted or substituted $C_{1-12}$ alkyl radical, or an unsubstituted or substituted $C_{6-22}$ aryl radical. Examples of carbonic acid diesters include, but are not limited to, ditolyl carbonate, m-cresyl carbonate, dinaphthyl carbonate, diphenyl carbonate, diethyl carbonate, dimethyl carbonate, dibutyl carbonate, dicyclohexyl carbonate, and combinations thereof. Diphenyl carbonate is widely used as a carbonic acid diester due to its low cost and ready availability on a commercial scale. Use of activated aromatic carbonates that are more reactive than diphenyl carbonate is also contemplated. Specific non-limiting examples of activated aromatic carbonates include bis(o-methoxycarbonylphenyl)carbonate, bis(o-chlorophenyl)carbonate, bis(o-nitrophenyl)carbonate, bis(o-acetylphenyl)carbonate, bis(o-phenylketonephenyl)carbonate, bis(o-formylphenyl)carbonate. Unsymmetrical combinations of these structures are also contemplated. Exemplary ester-substituted diaryl carbonates include, but are not limited to, bis(methylsalicyl)carbonate (CAS Registry No. 82091-12-1) (also known as BMSC or bis(o-methoxycarbonylphenyl) carbonate), bis(ethyl salicyl)carbonate, bis(propyl salicyl) carbonate, bis(butylsalicyl) carbonate, bis(benzyl salicyl) carbonate, bis(methyl 4-chlorosalicyl)carbonate, and the like. In some embodiments, BMSC is used in the melt transesterification process.

The melt transesterification process is generally carried out by combining a catalyst, the carbonic acid diester of formula (IX), the phthalimidine compound of formula (I), and optionally a dihydroxy comonomer; and mixing the reaction mixture under reactive conditions for a time period effective to produce the polycarbonate product. Exemplary melt transesterification catalysts include alkali metal compounds, alkaline earth metal compounds, tetraorganoammonium compounds, tetraorganophosphonium compounds, and combinations comprising at least one of the foregoing catalysts. Specific examples of alkali metal compounds or alkaline earth metal compounds include, but are not limited to, sodium hydroxide, potassium hydroxide, calcium hydroxide, magnesium hydroxide, sodium bicarbonate, potassium bicarbonate, sodium carbonate, potassium carbonate, lithium carbonate, sodium acetate, potassium acetate, sodium stearate, potassium stearate, sodium hydroxyborate, sodium phenoxyborate, sodium benzoate, potassium benzoate, lithium benzoate, disodium hydrogen phosphate, dipotassium hydrogen phosphate, dilithium hydrogen phosphate, disodium salts, dipotassium salts, and dilithium salts of bisphenol A, and sodium salts, potassium salts, lithium salts of phenol, and the like. Specific examples of tetraorganoammonium compounds and tetraorganophosphonium compounds include, but are not limited to tetramethylammonium hydroxide, tetrabutylammonium hydroxide, tetraethylphosphonium hydroxide, tetrabutylphosphonium acetate, tetrabutylphosphonium hydroxide, and the like.

In some embodiments, the catalyst is tetrabutylphosphonium acetate. In an alternative embodiment, the catalyst comprises a mixture of an alkali metal salt or alkaline earth metal salt with at least one quaternary ammonium compound, at least one quaternary phosphonium compound, or a mixture thereof. For example, the catalyst can be a mixture of sodium hydroxide and tetrabutylphosphonium acetate. In another embodiment, the catalyst is a mixture of sodium hydroxide and tetramethylammonium hydroxide. In yet another embodiment, the catalyst comprises the salt of a non-volatile inorganic acid, for example alkali metal salts of phosphites; alkaline earth metal salts of phosphites; alkali metal salts of phosphates; and alkaline earth metal salts of phosphates, including but not limited to $NaH_2PO_3$, $NaH_2PO_4$, $Na_2H_2PO_3$, $KH_2PO_4$, $CsH_2PO_4$, $Cs_2H_2PO_4$, or a mixture thereof. In some embodiments, the transesterification catalyst comprises both the salt of a non-volatile acid and a basic co-catalyst such as an alkali metal hydroxide. This concept is exemplified by the use of a combination of $NaH_2PO_4$ and sodium hydroxide as the transesterification catalyst.

Any of the catalysts disclosed above can be used as combinations of two or more substances. Moreover, the catalyst can be added in a variety of forms. For example, the catalyst can be added as a solid as a powder, or it can be dissolved in a solvent, for example, in water or alcohol. The total catalyst composition can be about $1 \times 10^{-7}$ to about $2 \times 10^{-3}$ moles, and in other embodiments, about $1 \times 10^{-6}$ to about $4 \times 10^{-4}$ moles, for each mole of the combination of, for example, the purified PPPBP and the aromatic dihydroxy comonomer.

The progress of the polymerization reaction can be monitored by measuring the melt viscosity or the weight average molecular weight of the reaction mixture using techniques known in the art such as gel permeation chromatography. These properties can be measured by taking discreet samples or can be measured on-line. After the desired melt viscosity or molecular weight is reached, the final polycarbonate product can be isolated from the reactor in a solid or molten form. The method of making polycarbonates as described in the preceding sections can be made in a batch or a continuous process.

In some embodiments, the melt-polymerized polycarbonate is prepared in an extruder in the presence of one or more catalysts. The reactants for the polymerization reaction can be fed to the extruder in powder or molten form. In some embodiments, the reactants are dry blended prior to addition to the extruder. The extruder can be equipped with pressure reducing devices (e.g., vents) that serve to remove the activated phenol byproduct and thus drive the polymerization reaction toward completion. The molecular weight of the polycarbonate product can be manipulated by controlling, among other factors, the feed rate of the reactants, the type of extruder, the extruder screw design and configuration, the residence time in the extruder, the reaction temperature, and the pressure reducing techniques present on the extruder. The molecular weight of the polycarbonate product can also depend upon the structures of the reactants and the catalyst employed. Many different screw designs and extruder configurations are commercially available that use single screws, double screws, vents, back flight and forward flight zones, seals, side-streams, and sizes.

Alternatively, the polycarbonates can be prepared by an interfacial polymerization process. Although the reaction conditions for interfacial polymerization can vary, an exemplary process generally involves dissolving or dispersing a dihydric phenol reactant in aqueous caustic soda or potash, adding the resulting mixture to a water-immiscible solvent medium, and contacting the reactants with a carbonate precursor in the presence of a catalyst such as triethylamine or a phase transfer catalyst, under controlled pH conditions, e.g., about 8 to about 12. The most commonly used water immiscible solvents include methylene chloride, 1,2-dichloroethane, chlorobenzene, toluene, and the like.

Exemplary carbonate precursors for interfacial polymerization include a carbonyl halide such as carbonyl bromide or carbonyl chloride, or a haloformate such as a bishaloformates of a dihydric phenol (e.g., the bischloroformates of bisphenol A, hydroquinone, or the like) or a glycol (e.g., the bishaloformate of ethylene glycol, neopentyl glycol, polyethylene glycol, or the like). Combinations comprising at least one of the foregoing types of carbonate precursors can also be used. In an exemplary embodiment, an interfacial polymerization reaction to form carbonate linkages uses phosgene as a carbonate precursor, and is referred to as a phosgenation reaction.

Among the phase transfer catalysts that can be used for interfacial polymerization are tetraorganoammonium compounds and tetraorganophosphonium compounds of the formula $(R^3)_4Q^+X$, wherein each $R^3$ is the same or different, and is a $C_{1-10}$ alkyl group; Q is a nitrogen or phosphorus atom; and X is a halogen atom or a $C_{1-8}$ alkoxy group or $C_{6-18}$ aryloxy group. Exemplary phase transfer catalysts include, for example, $[CH_3(CH_2)_3]_4NX$, $[CH_3(CH_2)_3]_4PX$, $[CH_3(CH_2)_5]_4NX$, $[CH_3(CH_2)_6]_4NX$, $[CH_3(CH_2)_4]_4NX$, $CH_3[CH_3(CH_2)_3]_3NX$, and $CH_3[CH_3(CH_2)_2]_3NX$, wherein X is Cl$^-$, Br$^-$, a $C_{1-8}$ alkoxy group or a $C_{6-18}$ aryloxy group. An effective amount of a phase transfer catalyst can be about 0.1 to about 10 wt % based on the weight of bisphenol in the phosgenation mixture. In another embodiment an effective amount of phase transfer catalyst can be about 0.5 to about 2 wt % based on the weight of bisphenol in the phosgenation mixture.

All types of polycarbonate end groups are contemplated as being useful in the polycarbonate composition, provided that such end groups do not significantly adversely affect desired properties of the compositions. Branched polycarbonate blocks can be prepared by adding a branching agent during polymerization. A chain stopper (also referred to as a capping agent) can be included during polymerization. The chain stopper limits molecular weight growth rate, and so controls molecular weight in the polycarbonate. Exemplary chain stoppers include certain mono-phenolic compounds, mono-carboxylic acid chlorides, or mono-chloroformates.

The interfacial method described above can be suitably adapted to produce polycarbonates through the intermediate formation of 2-aryl-3,3-bis(4-hydroxyaryl)phthalimidine bischloroformate. This method is sometimes called the bischloroformate polymerization method. In some embodiments, the method comprises reacting a 2-aryl-3,3-bis(4-hydroxyaryl)phthalimidine with phosgene in an organic solvent, and then reacting the bischloroformate either with a 2-aryl-3,3-bis(4-hydroxyaryl)phthalimidine, or an aromatic dihydroxy compound in the presence of an acid acceptor and an aqueous base to form the polycarbonate. The interfacial polymerization method and the bischloroformate polymerization method can be carried in a batch or a continuous mode using one or more reactor systems. To carry out the process in a continuous mode, one or more continuous reactors, such as for example, a tubular reactor can be used. In some embodiments, the continuous method comprises introducing into a tubular reactor system phosgene, at least one solvent (example, methylene chloride), at least one bisphenol, aqueous base, and optionally one or more catalysts (example, a trialkylamine) to form a flowing reaction mixture. The flowing mixture is then passed through the tubular reactor system until substantially all of the phosgene has been consumed. The resulting mixture is next treated with a mixture comprising an aqueous base, at least one endcapping agent, optionally one or more solvents, and at least one catalyst. The endcapped polycarbonate thus formed is continuously removed from the tubular reactor system.

The processes disclosed herein can advantageously be used to prepare, for example, PPPBP homopolycarbonate and copolycarbonates having a weight average molecular weight (Mw) of about 3,000 to about 150,000 Daltons and a glass transition temperature (Tg) of about 80° C. to about 300° C. The number average molecular weights (Mn) of the homopolycarbonate and copolycarbonates can be from about 1,500 to about 75,000 Daltons.

Polymers comprising structural units derived from the phthalimidines, in particular PPPBP can be used to manufacture polymer blends comprising the polymer and at least one other thermoplastic polymer. The at least one other thermoplastic polymer includes vinyl polymers, acrylic polymers, polyacrylonitrile, polystyrenes, polyolefins, polyesters, polyurethanes, polyamides, polysulfones, polyimides, polyetherimides, polyphenylene ethers, polyphenylene sulfides, polyether ketones, polyether ether ketones, ABS polymers, polyethersulfones, poly(alkenylaromatic) polymers, polybutadiene, polyacetals, polycarbonates, polyphenylene ethers, ethylene-vinyl acetate copolymers, polyvinyl acetate, liquid crystal polymers, ethylene-tetrafluoroethylene copolymer, aromatic polyesters, polyvinyl fluoride, polyvinylidene fluoride, polyvinylidene chloride, tetrafluoroethylene, polycarbonate-polyorganosiloxane block copolymers, copolymers comprising aromatic ester, estercarbonate, and carbonate repeat units, and combinations comprising at least one of the foregoing polymers.

The polymers and polymer blends described hereinabove are valuable for producing articles. In some embodiments, an article comprises a polymer comprising structural units derived from a 2-aryl-3,3-bis(4-hydroxyaryl)phthalimidine of formula (I) prepared by following the process described above.

Polymers, particularly polycarbonate homopolymers and copolymers comprising structural units derived from the high purity 2-aryl-3,3-bis(4-hydroxyaryl)phthalimidine in general, and PPPBP in particular exhibit lower visual coloration. As such, these polycarbonate polymers are useful for producing articles having a number of useful properties, including lower visual color, among others. The polycarbonate homopolymers and copolymers have high glass transition temperatures of higher than or equal to about 180° C. One of the unique properties of these polycarbonates, especially those that have glass transition temperatures of greater than or equal to about 180° C. is that during melt processing they exhibit a shear-thinning behavior. That is, the polymers have the ability to flow under an applied shear. Therefore, standard melt processing equipment used for BPA polycarbonates can advantageously be used for producing articles. The polycarbonates also have high transparency, as measured by percent light transmission, of greater than or equal to about 85 percent.

In addition to the polymer, the thermoplastic compositions comprising the polymers can include various additives ordinarily incorporated into polymer compositions of this type, with the proviso that the additive(s) are selected so as to not significantly adversely affect the desired properties of the thermoplastic composition, in particular low color. Such additives can be mixed at a suitable time during the mixing of the components for forming the composition. The additive can be soluble or non-soluble in polycarbonate. The additive composition can include an impact modifier, flow modifier, filler (e.g., a particulate polytetrafluoroethylene (PTFE), glass, carbon, mineral, or metal), reinforcing agent (e.g., glass fibers), antioxidant, heat stabilizer, light stabilizer, ultraviolet (UV) light stabilizer, UV absorbing additive, plasticizer, lubricant, release agent (such as a mold release agent), antistatic agent, anti-fog agent, antimicrobial agent, colorant (e.g., a dye or pigment), surface effect additive, radiation stabilizer, flame retardant, anti-drip agent (e.g., a PTFE-encapsulated styrene-acrylonitrile copolymer (TSAN)), or a combination comprising at least one or more of the foregoing. For example, a combination of a heat stabilizer, mold release agent, and ultraviolet light stabilizer can be used. In general, the additives are used in the amounts generally known to be effective. For example, the total amount of the additive composition (other than any impact modifier, filler, or reinforcing agent) can be 0.001 to 10.0 wt %, or 0.01 to 5 wt %, each based on the total weight of the polymer in the composition.

The methods described herein are further illustrated by the following non-limiting examples.

EXAMPLES

Example 1 (Comparative)

PPPBP was prepared in accordance with the procedures of U.S. Pat. No. 8,809,486, wherein the reaction mixture was subjected to azeotropic distillation of water at 100 to 120° C. for 2-3 hours (h), then at 145° C. To precipitate the product, the reaction mixture was allowed to cool to 100-110° C., and 250 ml of 10 wt % aqueous HCl was added into the reaction mixture followed by stirring for 1 hour. A precipitate was formed, filtered out, washed with water until free from chloride, and dried, resulting in crude PPPBP, PP conversion: >99% (HPLC wt %); PPPBP purity: 98% (HPLC wt %); aminophenol (AP): 0.29% (HPLC wt %)

Example 2

First, 8.3 ml of 35 wt % aqueous HCl (0.079 mol) and 28.85 ml (0.316 mol) of aniline were combined in a 250-ml 3-neck round bottom flask fitted with an overhead stirrer, a thermowell and a condenser with Dean-Stark apparatus. The reaction mixture was heated to about 120° C. (internal temperature), for about an hour to remove water. The reaction mixture was then cooled to about 50-60° C., then 25 g (0.079 mol) of phenolphthalein and pyridine co-catalyst (0.009-0.08 mol) as shown in Table 1 were added. The reaction mixture was heated to 145° C. (internal temperature) for 48-30 h and allowed to cool to 100-110° C. Next, 108 ml of 10% aqueous HCl was then added into the reaction mixture followed by stirring for 1 h. A precipitate was formed, filtered out, washed with water until free from chloride, and dried, resulting in crude PPPBP. The results for different concentrations of the co-catalyst are provided in Table 1.

TABLE 1

| No. | Catalyst | Co-catalyst | Equiv.* | PP/Aniline (mol.) | Reaction mass Temp. (° C.) | Time (h.) | PP conversion** | PPPBP selectivity** | AP** |
|---|---|---|---|---|---|---|---|---|---|
| 1 | Aniline•HCl | Pyridine | 0.08 | 4 | 145 | 48 | >99 | 97 | 0.17 |
| 2 | Aniline•HCl | Pyridine | 0.02 | 4 | 145 | 35 | >99 | 97 | 0.13 |
| 3 | Aniline•HCl | Pyridine | 0.017 | 4 | 145 | 30 | 98 | 96 | 0.09 |
| 4 | Aniline•HCl | Pyridine | 0.013 | 4 | 145 | 35 | 98 | 97.7 | 0.09 |
| 5 | Aniline•HCl | Pyridine | 0.009 | 4 | 145 | 30 | 88.5 | 87.5 | 0.055 |

*Equivalents of co-catalyst with respect to PP
**Determined based on percent area of HPLC trace The results show that use of the pyridine co-catalyst can reduce the AP percentage at all concentrations, even at a shorter reaction time, compared to the reaction carried out without the co-catalyst (0.29% in Comparative Example 1).

Example 3 (Comparative)

The experiment described in Example 1 (no co-catalyst) is repeated at higher temperatures (155, 165, 170, and 175° C.) for shorter reaction times (17-7 h). The predicted or experimental values for phenolphthalein (PP) conversion and aminophenol (AP) impurity formation are provided in Table 2.

TABLE 2

| No. | Catalyst | Co-catalyst | PP/Aniline (mol.) | Reaction mass Temp. (° C.) | Time (h.) | PP conversion (HPLC area %) | AP (HPLC area %) |
|---|---|---|---|---|---|---|---|
| 1 | Aniline•HCl | — | 4 | 155 | 17 | 91.7 | 0.33 |
| 2 | Aniline•HCl | — | 4 | 155 | 10 | 89.0 (Experimental) | 0.11 (Experimental.) |
| 3 | Aniline•HCl | — | 4 | 165 | 7 | 79.6 | 0.38 |
| 4 | Aniline•HCl | — | 4 | 175 | 7 | 91 | 1 |

The results show that the amount of aminophenol is expected to increase as the reaction temperature increases and the reaction time decreases.

Example 4

The experiment described in Example 2 was repeated at higher temperatures (155, 165, 170, and 175° C.) for shorter reaction times (17 to 5 h) and with different concentrations of pyridine co-catalyst (0.013-0.04 moles.). The results are shown in Table 3.

TABLE 3

| No. | Catalyst | Co-catalyst | PP* | PP/Aniline (mol) | Reaction mass Temp. (° C.) | Time (h) | PP conversion** | PPPB selectivity** | AP** |
|---|---|---|---|---|---|---|---|---|---|
| 1 | Aniline•HCl | Pyridine | 0.02 | 4 | 155 | 17 | 98.5 | 98 | 0.14 |
| 2 | Aniline•HCl | Pyridine | 0.02 | 4 | 155 | 8 | 82 | 81.6 | 0.078 |
| 3 | Aniline•HCl | Pyridine | 0.04 | 4 | 155 | 8 | 78.4 | 78 | 0.063 |
| 4 | Aniline•HCl | Pyridine | 0.02 | 4 | 155 | 10 | 88 | 87.4 | 0.1 |
| 5 | Aniline•HCl | Pyridine | 0.02 | 4 | 155 | 12 | 91 | 90.23 | 0.24 |
| 6 | Aniline•HCl | Pyridine | 0.02 | 4 | 165 | 7 | 86.5 | 86 | 0.18 |
| 7 | Aniline•HCl | Pyridine | 0.02 | 4 | 175 | 7 | >99 | 98 | 0.75 |
| 8 | Aniline•HCl | Pyridine | 0.02 | 4 | 175 | 5 | 97.5 | 96.1 | 0.66 |
| 9 | Aniline•HCl | Pyridine | 0.017 | 4 | 175 | 6 | 98.60 | 97.1 | 1.0 |
| 10 | Aniline•HCl | Pyridine | 0.02 | 4 | 170 | 7 | 96 | 95.5 | 0.33 |
| 11 | Aniline•HCl | Pyridine | 0.04 | 4 | 170 | 5 | 91 | 90.2 | 0.24 |
| 12 | Aniline•HCl | Pyridine | 0.02 | 4 | 170 | 8 | 98.7 | 97.4 | 0.8 |
| 13 | Aniline•HCl | Pyridine | 0.017 | 4 | 170 | 8 | 98.3 | 97.4 | 0.55 |
| 14 | Aniline•HCl | Pyridine | 0.013 | 4 | 170 | 8 | 98.5 | 97.4 | 0.66 |
| 15 | Aniline•HCl | Pyridine | 0.013 | 4 | 170 | 6 | 91.8 | 91.2 | 0.32 |

*Equivalents of co-catalyst with respect to PP
**Determined based on percent area of HPLC trace The results show that a pyridine co-catalyst is used, the aminophenol percent at a given reaction temperature and reaction time is decreased as compared to the experiments described in Table 2.

Example 5

The experiment described in Example 2 was repeated using 0.017 and 0.02 moles of other amines as co-catalysts. The results are provided in Table 4.

TABLE 4

| No. | Catalyst | Co-catalyst | PP* | PP/Aniline (mol) | Reaction mass Temp. (° C.) | Time (h) | PP conversion** | PPPB selectivity* | AP** |
|---|---|---|---|---|---|---|---|---|---|
| 1 | Aniline•HCl | Pyridine | 0.017 | 4 | 145 | 30 | 98 | 96 | 0.09 |
| 2 | Aniline•HCl | DMAP | 0.02 | 4 | 145 | 30 | 98.5 | 96 | 0.12 |
| 3 | Aniline•HCl | Imidazole | 0.017 | 4 | 145 | 30 | 92 | 90 | 0.089 |

*Equivalents of co-catalyst with respect to PP
**Determined based on percent area of HPLC trace The results show that other co-catalysts can be used to reduce the amount of AP compared to a reaction performed without the use of a co-catalyst.

The methods and polymers are further illustrated by the following embodiments, which are non-limiting.

Embodiment 1: A method for the manufacture of a 2-aryl-3,3-bis(hydroxyaryl)phthalimidine of formula (I)

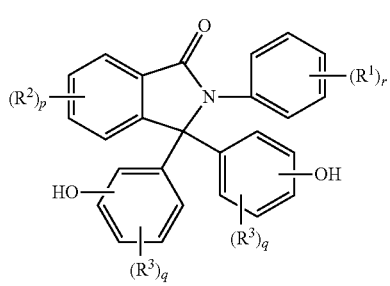

the method comprising heating a reaction mixture comprising a phenolphthalein compound of formula (II)

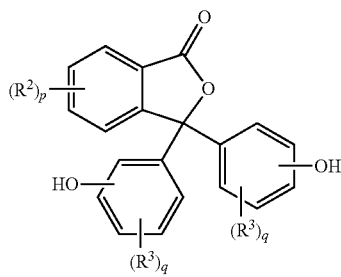

an a primary arylamine of formula (III)

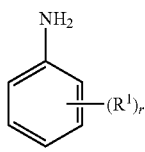

in the presence of an acid catalyst, and a heterocyclic aromatic amine co-catalyst,
to form the 2-aryl-3,3-bis(hydroxyaryl)phthalimidine of formula (I), wherein in formulas (I), (II), and (III), each occurrence of $R^1$ is independently a phenyl or a $C_{1-25}$ hydrocarbyl, preferably a phenyl or a $C_{1-6}$ alkyl, more preferably a $C_{1-3}$ alkyl, each occurrence of $R^2$ and $R^3$ is independently a $C_{1-25}$ hydrocarbyl or halogen, preferably a $C_{1-6}$ alkyl, more preferably a $C_{1-3}$ alkyl, and r, p, and q are each independently 0 to 4, more preferably 0 or 1, preferably 0.

Embodiment 2: The method of Embodiment 1, wherein the as-synthesized 2-aryl-3,3-bis(hydroxyaryl)phthalimidine of formula (I) comprises 500 to 8000 parts per million, preferably 800 to 5000 parts per million, more preferably from 400 to 1400 parts per million of an aminophenol.

Embodiment 3: The method of any one or more of Embodiments 1 to 2, wherein the 2-aryl-3,3-bis(hydroxyaryl)phthalimidine of formula (I) comprises zero to 1000 parts per million of the phenolphthalein compound of formula (II), preferably zero to 500 parts per million of the phenolphthalein compound of formula (II).

Embodiment 4: The method of any one or more of Embodiments 1 to 3, wherein the primary arylamine is aniline.

Embodiment 5: The method of any one or more of Embodiment 1 to 4, wherein the heterocyclic aromatic amine co-catalyst has 5 to 10, preferably 5 to 6 atoms in the ring, and is unsubstituted or substituted with a halogen, nitro, cyano, $C_{1-6}$ alkyl, $C_{3-6}$ cycloalkyl, $C_{2-6}$ alkenyl, $C_{2-6}$ alkynyl, $C_{1-6}$ alkoxy, $C_{1-6}$ alkoxycarbonyl, $C_{6-10}$ aryl, $C_{6-10}$ aryloxy, $C_{7-10}$ alkylarylene, $C_{7-10}$ arylalkylene, —$NR'_2$ wherein each R' is the same or different and is a hydrogen, $C_{1-6}$ alkyl, $C_{6-10}$ aryl, $C_{7-10}$ alkylarylene, or $C_{7-10}$ arylalkylene, or two adjacent carbon atoms are substituted with a divalent moiety having from 3 to 4 atoms to form a fused aromatic ring wherein 1 or 2 of the atoms can be a nitrogen, or a combination comprising at least one of the foregoing substituents, preferably wherein the ring is unsubstituted or substituted with a $C_{1-3}$ alkyl, $C_{1-3}$ alkoxy, $C_{1-3}$ alkoxycarbonyl, $C_{6-10}$ aryl, $C_{6-10}$ aryloxy, $C_{7-10}$ alkylarylene, $C_{7-10}$ arylalkylene, $NR'_2$ wherein each R' is the same or different and is a hydrogen, $C_{1-3}$ alkyl, $C_6$ aryl, $C_{7-10}$ alkylarylene, or $C_{7-10}$ arylalkylene, or two adjacent carbon atoms are substituted with a divalent moiety having from 3 to 4 carbon atoms to form a fused aromatic ring, or a combination comprising at least one of the foregoing substituents; preferably wherein the heterocyclic aromatic amine is a pyrrole, an imidazole, a pyridine, an oxazole, an isoxazole, a thiazole, an azocine, an azecine, a quinolone, an isoquinoline, a purine, a carbazole, or a pyrimidine, wherein one or more of the carbon atoms in the ring may be substituted with a heteroatom, and wherein each of the foregoing can be unsubstituted or substituted with a halogen, nitro, cyano, $C_{1-6}$ alkyl, $C_{2-6}$ alkenyl, $C_{2-6}$ alkynyl, $C_{1-6}$ alkoxy, $C_{1-6}$ alkoxycarbonyl, $C_{6-10}$ aryl, $C_{6-10}$ aryloxy, $C_{7-10}$ alkylarylene, $C_{7-10}$ arylalkyl, $C_{7-10}$ arylalkylene, —$NR'_2$ wherein each W is the same or different and is a hydrogen, $C_{1-6}$ alkyl, $C_{6-10}$ aryl, $C_{7-10}$ alkylarylene, or $C_{7-10}$ arylalkylene, or two adjacent carbon atoms are substituted with a divalent moiety having from 3 to 4 carbon atoms to form a fused aromatic ring, or a combination comprising at least one of the foregoing, preferably wherein the ring is unsubstituted or substituted with a $C_{1-3}$ alkyl, $C_{1-3}$ alkoxy, $C_{1-3}$ alkoxycarbonyl, $C_{6-10}$ aryl, $C_{6-10}$ aryloxy, $C_{7-10}$ alkylarylene, $C_{7-10}$ arylalkylene, —$NR'_2$ wherein each R' is the same or different and is a hydrogen, $C_{1-3}$ alkyl, $C_6$ aryl, $C_{7-10}$ alkylarylene, or $C_{7-10}$ arylalkylene, or two adjacent carbon atoms are substituted with a divalent moiety having from 3 to 4 carbon atoms to form a fused aromatic ring, or a combination comprising at least one of the foregoing; preferably wherein the heterocyclic aromatic amine is unsubstituted pyridine, unsubstituted imidazole, or a 4-dimethyl-aminopyridine.

Embodiment 6: The method of any one or more of Embodiments 1 to 5, wherein the acid catalyst is a mineral acid, preferably hydrochloric acid.

Embodiment 7: The method of any one or more of Embodiments 1 to 6, wherein the heterocyclic aromatic amine is present at a concentration of 0.005-0.5 molar equivalents of the phenolphthalein compound of formula (II), preferably a concentration of 0.01 to 0.2 molar equivalents of the phenolphthalein compound of formula (II).

Embodiment 8: The method of any one or more of Embodiments 1 to 7, wherein the acid catalyst is present at a concentration of 0.5-1.5 molar equivalents of the phenolphthalein compound of formula (II).

Embodiment 9: The method of any one or more of Embodiments 1 to 8, wherein the primary arylamine is present at a concentration of 3.0-5.0 molar equivalents of the phenolphthalein compound of formula (II).

Embodiment 10: The method of any one or more of Embodiment 1 to 9, wherein the heating is from 135-180° C., preferably from 140-175° C., more preferably from 135 to 150° C.

Embodiment 11: The method of any one or more of Embodiments 1 to 10, wherein the heating is for 8 to 40 hours, preferably 8 to 30 hours, more preferably 8 to 17 hours.

Embodiment 12: The method of any one or more of Embodiments 1 to 11, wherein the heating is for 10 to 40 hours at 135 to 150° C., and provides the as-synthesized 2-aryl-3,3-bis(hydroxyaryl)phthalimidine of formula (I) having an aminophenol content of 400 to 1400 parts per million.

Embodiment 13: The method of any one or more of Embodiments 1 to 12, comprising adding the acid catalyst and the primary arylamine to a solvent to form an initial composition; removing water from the initial composition to provide a reduced water composition; and adding the phenolphthalein compound of formula (II) and the co-catalyst to the reduced water composition to provide the reaction mixture.

Embodiment 14: The method of any one or more of Embodiments 1 to 13, further comprising precipitating the phthalimidine of formula (I) from the reaction mixture to provide a crude 2-aryl-3,3-bis(hydroxyaryl)phthalimidine of formula (I).

Embodiment 15: The method of any one or more of Embodiments 1 to 14, further comprising purifying the 2-aryl-3,3-bis(hydroxyaryl)phthalimidine of formula (I).

Embodiment 16: The method of any one or more of Embodiments 1 to 15, wherein the 2-aryl-3,3-bis(hydroxyaryl)phthalimidine of formula (I) is of formula (IA)

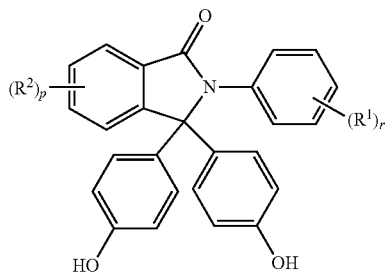

(IA)

wherein $R^1$ is a hydrogen or a $C_{1-3}$ alkyl, $R^2$ is a $C_{1-3}$ alkyl or a halogen, p is 0 or 1, and r is 0 or 1; wherein $R^1$ is a hydrogen or a $C_{1-3}$ alkyl, $R^2$ is a $C_{1-3}$ alkyl or a halogen, p is 0 or 1, and r is 0 or 1; the phenolphthalein compound of formula (II) is phenolphthalein; the heterocyclic aromatic amine is unsubstituted pyridine, unsubstituted imidazole, or a 4-dimethyl-aminopyridine; the acid catalyst is a mineral acid; and the primary arylamine is aniline.

Embodiment 17: The method of any one or more of Embodiments 1 to 16, wherein the acid catalyst is hydrochloric acid, the primary arylamine is aniline, the phenolphthalein compound is phenolphthalein, and the heterocyclic aromatic amine co-catalyst is pyridine.

Embodiment 18: The method of any one or more of the Embodiments 1 to 17, wherein the 2-aryl-3,3-bis(hydroxyaryl)phthalimidine of formula (I) is of formula (IV):

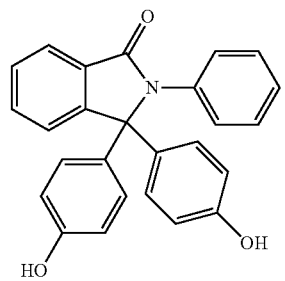

(IV)

the phenolphthalein compound of formula (II) is phenolphthalein;
the primary arylamine of formula (III) is aniline;
the acid catalyst is hydrochloric acid; and
the heterocyclic aromatic amine co-catalyst is pyridine.

Embodiment 19: A 2-aryl-3,3-bis(4-hydroxyaryl) phthalimidine composition, comprising an as-synthesized phthalimidine of formula (I)

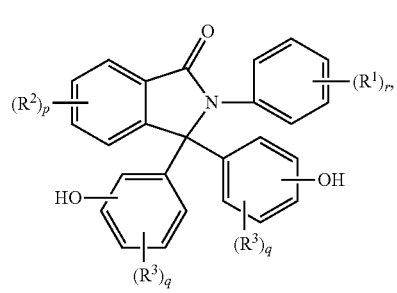

(I)

wherein each occurrence of $R^1$ is independently a phenyl or $C_{1-25}$ hydrocarbyl, preferably a phenyl or a $C_{1-6}$ alkyl, more preferably a $C_{1-3}$ alkyl, each occurrence of $R^2$ and $R^3$ is independently $C_{1-25}$ hydrocarbyl or halogen, preferably a $C_{1-6}$ alkyl, more preferably a $C_{1-3}$ alkyl, and r, p, and q are each independently 0 to 4, more preferably 0 or 1, preferably 0; 500 to 8000 parts per million of an aminophenol, preferably 800 to 5000, more preferably from 400 to 1400 parts per million of an aminophenol; and zero to 1000 parts per million of phenolphthalein, preferably zero to 500 parts per million of phenolphthalein.

Embodiment 20: A method for the manufacture of a polycarbonate, comprising manufacturing the 2-aryl-3,3-bis (4-hydroxyaryl) phthalimidine of formula (I) in accordance with any one or more of Embodiments 1 to 18; and polymerizing the 2-aryl-3,3-bis(4-hydroxyaryl) phthalimidine of formula (I) in the presence of a carbonate source.

The term "hydrocarbyl" is defined herein as a monovalent moiety formed by removing a hydrogen atom from a hydrocarbon. Representative hydrocarbyls are alkyl groups having 1 to 25 carbon atoms, such as, for example, methyl, ethyl, propyl, butyl, pentyl, hexyl, heptyl, octyl, nonyl, undecyl, decyl, dodecyl, octadecyl, nonadecyl, eicosyl, heneicosyl, docosyl, tricosyl, and the isomeric forms thereof; aryl groups having 6 to 25 carbon atoms, such as ring-substituted and ring-unsubstituted forms of phenyl, tolyl, xylyl, naphthyl, biphenyl, tetraphenyl, and the like; arylalkyl groups having 7 to 25 carbon atoms, such as ring-substituted and ring-unsubstituted forms of benzyl, phenethyl, phenpropyl, phenbutyl, naphthoctyl, and the like; and cycloalkyl groups, such as cyclopropyl, cyclobutyl, cyclopentyl, cyclohexyl, cycloheptyl, cyclooctyl, and the like. The term "aryl" as used herein refers to various forms of aryl groups that have been described hereinabove for the "hydrocarbyl" group. "Alkyl" refers to a straight or branched chain, saturated monovalent hydrocarbon group. Unless otherwise indicated, each of the foregoing groups can be unsubstituted or substituted, provided that the substitution does not significantly adversely affect synthesis, stability, or use of the compound. The term "substituted" as used herein means that at least one hydrogen on the designated atom or group is replaced with another group, provided that the designated atom's normal valence is not exceeded. When the substituent is oxo (i.e., =O), then two hydrogens on the atom are replaced. Combinations of substituents and/or variables are permissible provided that the substitutions do not significantly adversely affect synthesis or use of the compound. Exemplary groups that can be present on a "substituted" position include, but are not limited to, cyano; hydroxyl; nitro; azido; alkanoyl (such as a $C_{2-6}$ alkanoyl group such as acyl); carboxamido; $C_{1-6}$ or $C_{1-3}$ alkyl, cycloalkyl, alkenyl, and alkynyl (including groups having at least one unsaturated linkages and from 2 to 8, or 2 to 6 carbon atoms); $C_{1-6}$ or $C_{1-3}$ alkoxys; $C_{6-10}$ aryloxy such as phenoxy; $C_{1-6}$ alkylthio; $C_{1-6}$ or $C_{1-3}$ alkylsulfinyl; $C_{1-6}$ or $C_{1-3}$ alkylsulfonyl; aminodi($C_{1-6}$ or $C_{1-3}$) alkyl; $C_{6-12}$ aryl having at least one aromatic rings (e.g., phenyl, biphenyl, naphthyl, or the like, each ring either substituted or unsubstituted aromatic); $C_{7-19}$ arylalkyl having 1 to 3 separate or fused rings and from 6 to 18 ring carbon atoms; or arylalkoxy having 1 to 3 separate or fused rings and from 6 to 18 ring carbon atoms, with benzyloxy being an exemplary arylalkoxy.

The singular forms "a," "an," and "the" include plural referents unless the context clearly dictates otherwise. "Or" means "and/or." The modifier "about" used in connection with a quantity is inclusive of the stated value and has the meaning dictated by the context (e.g., includes the degree of error associated with measurement of the particular quantity).

The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. The suffix "(s)" is intended to include both the singular and the plural of the term that it modifies, thereby including at least one of that term (e.g., the colorant(s) includes at least one colorants). "Optional" or "optionally" means that the subsequently described event or circumstance may or may not occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

All publications, patents, and patent applications cited in this specification are herein incorporated by reference, and for any and all purposes, as if each individual publication, patent or patent application were specifically and individually indicated to be incorporated by reference. In the case of inconsistencies, the present disclosure will prevail.

While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

What is claimed is:

1. A method for the manufacture of a 2-aryl-3,3-bis (hydroxyaryl)phthalimidine of formula (I)

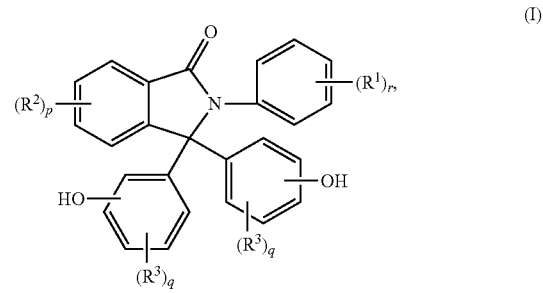

the method comprising heating a reaction mixture comprising a phenolphthalein compound of formula (II)

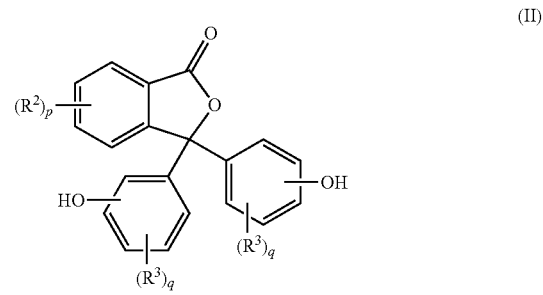

and a primary arylamine of formula (III)

in the presence of
an acid catalyst, and
a heterocyclic aromatic amine co-catalyst,
to form the 2-aryl-3,3-bis(hydroxyaryl)phthalimidine of formula (I), wherein in formulas (I), (II), and (III),
each occurrence of $R^1$ is independently a $C_{1-25}$ hydrocarbyl,
each occurrence of $R^2$ and $R^3$ is independently a $C_{1-25}$ hydrocarbyl or halogen, and
r, p, and q are each independently 0 to 4.

2. The method of claim 1, wherein the 2-aryl-3,3-bis (hydroxyaryl)phthalimidine of formula (I) comprises 500 to 8000 parts per million of an aminophenol.

3. The method of claim 1, wherein the 2-aryl-3,3-bis (hydroxyaryl)phthalimidine of formula (I) comprises zero to 1000 parts per million of the phenolphthalein compound of formula (II).

4. The method of claim 1, wherein the primary arylamine is aniline.

5. The method of claim 1, wherein the heterocyclic aromatic amine co-catalyst has 5 to 10 atoms in the ring, and is unsubstituted or substituted with a halogen, nitro, cyano, $C_{1-6}$ alkyl, $C_{3-6}$ cycloalkyl, $C_{2-6}$ alkenyl, $C_{2-6}$ alkynyl, $C_{1-6}$ alkoxy, $C_{1-6}$ alkoxycarbonyl, $C_{6-10}$ aryl, $C_{6-10}$ aryloxy, $C_{7-10}$ alkylarylene, $C_{7-10}$ arylalkylene, —$NR'_2$ wherein each R' is the same or different and is a hydrogen, $C_{1-6}$ alkyl, $C_{6-10}$ aryl, $C_{7-10}$ alkylarylene, or $C_{7-10}$ arylalkylene, or two adjacent carbon atoms are substituted with a divalent moiety having from 3 to 4 atoms to form a fused aromatic ring wherein 1 or 2 of the atoms can be a nitrogen, or a combination comprising at least one of the foregoing substituents.

6. The method of claim 1, wherein the acid catalyst is a mineral acid.

7. The method of claim 1, wherein the heterocyclic aromatic amine co-catalyst is present at a concentration of 0.005-0.5 molar equivalents of the phenolphthalein compound of formula (II).

8. The method of claim 1, wherein the acid catalyst is present at a concentration of 0.5-1.5 molar equivalents of the phenolphthalein compound of formula (II).

9. The method of claim 1, wherein the primary arylamine is present at a concentration of 3.0-5.0 molar equivalents of the phenolphthalein compound of formula (II).

10. The method of claim 1, wherein the heating is from 135 to 180° C.

11. The method of claim 1, wherein the heating is for 8 to 40 hours.

12. The method of claim 1, wherein the heating is for 10 to 40 hours at 135 to 150° C., and provides the 2-aryl-3,3-bis(hydroxyaryl)phthalimidine of formula (I) having an aminophenol content of 400 to 1400 parts per million.

13. The method of claim 1, further comprising
adding the acid catalyst and the primary arylamine to a solvent to form an initial composition;
removing water from the initial composition to provide a reduced water composition; and
adding the phenolphthalein compound of formula (II) and the heterocyclic aromatic amine co-catalyst to the reduced water composition to provide the reaction mixture.

14. The method of claim 1, further comprising precipitating the phthalimidine of formula (I) from the reaction mixture to provide a crude 2-aryl-3,3-bis(hydroxyaryl)phthalimidine of formula (I).

15. The method of claim 14, further comprising purifying the crude 2-aryl-3,3-bis(hydroxyaryl)phthalimidine of formula (I).

16. The method of claim 1, wherein the 2-aryl-3,3-bis(hydroxyaryl)phthalimidine of formula (I) is of formula (IA)

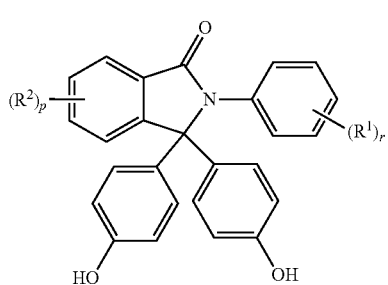

(IA)

wherein $R^1$ is a hydrogen or a $C_{1-3}$ alkyl, $R^2$ is a $C_{1-3}$ alkyl or a halogen, p is 0 or 1, and r is 0 or 1;
the phenolphthalein compound of formula (II) is phenolphthalein;
the heterocyclic aromatic amine co-catalyst is unsubstituted pyridine, unsubstituted imidazole, or a 4-dimethyl-aminopyridine;
the acid catalyst is a mineral acid; and
the primary arylamine of formula (III) is aniline.

17. The method of claim 1, wherein the acid catalyst is hydrochloric acid, the primary arylamine of formula (III) is aniline, the phenolphthalein compound of formula (II) is phenolphthalein, and the heterocyclic aromatic amine co-catalyst is pyridine.

18. The method of claim 1, wherein the 2-aryl-3,3-bis(hydroxyaryl)phthalimidine of formula (I) is of formula (IV):

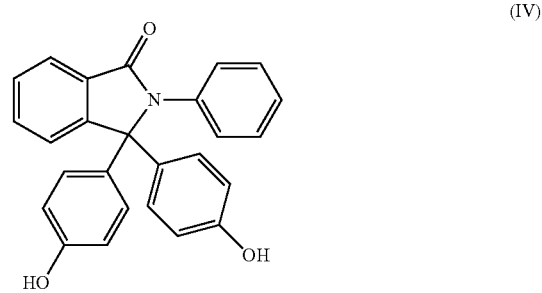 [SMILES: O=C1c2ccccc2C(c2ccc(O)cc2)(c2ccc(O)cc2)N1c1ccccc1]

(IV)

the phenolphthalein compound of formula (II) is phenolphthalein;
the primary arylamine of formula (III) is aniline;
the acid catalyst is hydrochloric acid; and
the heterocyclic aromatic amine co-catalyst is pyridine.

19. A 2-aryl-3,3-bis(4-hydroxyaryl) phthalimidine composition, comprising
a phthalimidine of formula (I)

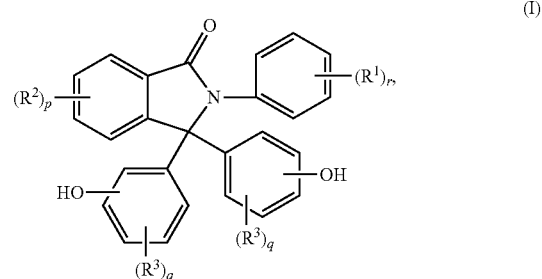

(I)

wherein
each occurrence of $R^1$ is independently a $C_{1-25}$ hydrocarbyl,
each occurrence of $R^2$ and $R^3$ is independently a $C_{1-25}$ hydrocarbyl or halogen, and
r, p, and q are each independently 0 to 4;
500 to 1200 parts per million of an aminophenol; and
zero to 1000 parts per million of a phenolphthalein compound of formula (II)

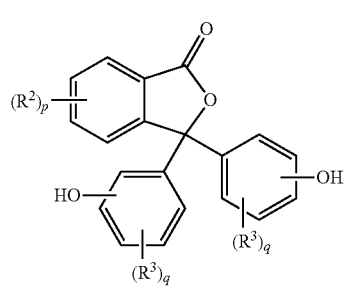 (II)

an acid catalyst and
a heterocyclic aromatic amine co-catalyst,
wherein the phthalimidine is manufactured in the presence of the acid catalyst and the heterocyclic aromatic amine co-catalyst.

20. A method for the manufacture of a polycarbonate, comprising
manufacturing the 2-aryl-3,3-bis(4-hydroxyaryl) phthalimidine of formula (I) in accordance with the method of claim 1; and
polymerizing the 2-aryl-3,3-bis(4-hydroxyaryl) phthalimidine of formula (I) in the presence of a carbonate source.

21. The composition of claim 19, wherein the phthalimidine of formula (I) is an as-synthesized phthalimidine comprising 500 to 1000 parts per million of an aminophenol.

* * * * *